United States Patent [19]

Beck et al.

[11] Patent Number: 5,470,699
[45] Date of Patent: Nov. 28, 1995

[54] HARDENING OF GELATIN-CONTAINING LAYERS

[75] Inventors: Anthony L. Beck; Julian M. Wallis; Martin D. Attwood, all of Harlow; Stephen Newman, Bishops Stortford, all of Great Britain

[73] Assignee: Minnesota Mining and Manufacturing Company, St. Paul, Minn.

[21] Appl. No.: 272,097

[22] Filed: Jul. 8, 1994

[30] Foreign Application Priority Data

Jul. 27, 1993 [GB] United Kingdom .................. 9315468

[51] Int. Cl.$^6$ .................................................. G03C 1/30
[52] U.S. Cl. ........................ 430/621; 430/202; 430/610; 430/623; 430/640
[58] Field of Search .................................... 430/621, 623, 430/537, 640, 610, 202

[56] References Cited

U.S. PATENT DOCUMENTS

| | | |
|---|---|---|
| 3,428,456 | 2/1969 | Grabhofer et al. . |
| 4,618,573 | 10/1986 | Okamura et al. . |
| 5,073,480 | 12/1991 | Kok et al. ............................ 430/621 |

FOREIGN PATENT DOCUMENTS

| | | |
|---|---|---|
| 1076629 | 7/1967 | European Pat. Off. . |
| 0524540 | 1/1993 | European Pat. Off. . |
| 49-118747 | 11/1974 | Japan . |
| 5-7044140 | 7/1980 | Japan . |
| 5-8113929A | 12/1981 | Japan . |
| 3-259242 | 3/1990 | Japan . |
| 3-259241 | 11/1991 | Japan . |
| 3-259243 | 11/1991 | Japan . |
| 4-157455 | 5/1992 | Japan . |
| 4-157453 | 5/1992 | Japan . |
| 4-157454 | 5/1992 | Japan . |
| 4-306645 | 10/1992 | Japan . |
| 4-306644 | 10/1992 | Japan . |
| 4-316039 | 11/1992 | Japan . |
| 5-34866 | 2/1993 | Japan . |
| 5-27358 | 2/1993 | Japan . |
| 5-61139 | 3/1993 | Japan . |
| 5-61138 | 3/1993 | Japan . |

*Primary Examiner*—Thorl Chea
*Attorney, Agent, or Firm*—Gary L. Griswold; Walter N. Kirn; Mark A. Litman

[57] ABSTRACT

Gelatin hardeners, suitable for use in hardening gelatin-containing photographic layers, of the formula:

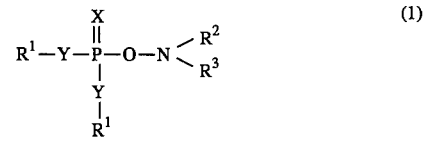

wherein:

X is a member selected from the group consisting of O and S or is absent, each Y independently is a member selected from the group consisting of O, S and a bond, each $R^1$ independently represents an aliphatic group of up to 10 carbon atoms or the two $R^1$ groups together represent the necessary atoms to complete a 5, 6 or 7-membered ring, —$NR^2R^3$ contains not more than 12 skeletal atoms and $R^2$ and $R^3$ are independently members of the group consisting of hydrogen, cyclic groups and acyclic groups or $R^2$ and $R^3$ together represent the necessary atoms to complete a heterocyclic ring.

21 Claims, No Drawings

HARDENING OF GELATIN-CONTAINING LAYERS

FIELD OF THE INVENTION

This invention relates to the hardening of gelatin-containing layers and in particular to the hardening of gelatin-containing photographic layers and to photographic elements containing such layers.

BACKGROUND TO THE INVENTION

The chemical crosslinking of gelatin is a critical part of producing photographically useful silver halide films. The crosslinking imparts numerous advantages on the coated film through reducing the degree of swelling of the emulsion layer in water, and by increasing the so-called 'melting point' of the gelatin. Improvements in physical characteristics include more resistance to scratching and reduced tendency to become soft or tacky. Suitable hardeners for use in gelatin-containing photographic layers should have no significant detrimental effects on other parameters of the film, e.g., sensitometry.

A number of gelatin crosslinkers are known and find use as hardeners in photographic applications. A commonly used hardener, particularly in photographic elements for Graphic Arts, is formaldehyde. This material is an effective gelatin crosslinker, but has a number of disadvantages which are increasingly of importance, such as the inter-related problems of toxicity and volatility (both in the factory and for the customer) and after-hardening effects. The latter means that it can take some time, often weeks, for the gelatin to reach its final hardness. Since the sensitometric properties of the film depend on film hardness, it is desirable for the hardening process to be complete soon after coating, preferably within one week, for quality control-purposes in the manufacturing plant.

Other hardening agents, such as vinyl sulphones, require elaborate multi-step syntheses for their production which increases the cost of the hardening agents. Also some gelatin hardeners can react with other compounds in the photographic construction, for example antihalation dyes and colour couplers making them unacceptable for use in many photographic elements.

A number of gelatin hardeners containing phosphorus are known.

JP 57044140 discloses pyridinium quaternary salts of substituted aliphatic phosphates:

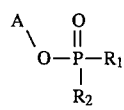

where A is a 1-alkyl or 1-aryl pyridinium or quinolinium quaternary salt residue.

JP 58-113929 also discloses the use of organophosphorus compounds of the following formula as gelatin hardeners:

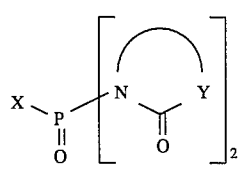

where X is halogen, Y is O, S, or $CH_2$:

U.S. Pat. No. 4668616 discloses the following triaminophosphonium salts as gelatin hardeners:

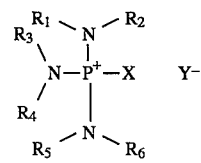

where X is a leaving group to be released on reaction of the compound with a nucleophilic reagent.

U.S. Pat. No. 5073480 discloses phosphate derivatives of the following formula as quick acting hardeners for proteinaceous gelatin materials:

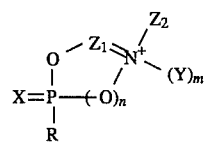

where $Z_1$ and $Z_2$ are alkyl, cycloalkyl or aryl, or $Z_1$ is alkylidene, or $Z_1$ and $Z_2$ together form a 5- or 6-membered heterocyclic ring; Y is alkyl, cycloalkyl or aryl; X is O or S; R is alkyl, cycloalkyl, aryl, alkoxy or aryloxy, alkylthio or arylthio, optionally substituted amino or 0; n is 0 or 1: m is 0 or 1, m being 0 if the nitrogen to which Y is attached is involved in a double bond.

JP 03259241 discloses, as gelatin hardeners, azido phosphorus compounds:

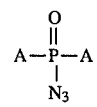

where A is optionally substituted aryloxy or

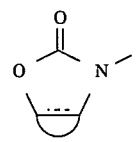

JP 03259242 discloses, as gelatin hardeners, phosphorus compounds:

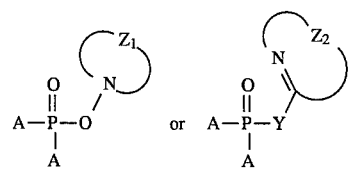

where Y is 0 or S; $Z_1$ and $Z_2$ are the atomic groupings required to complete heterocyclic rings; A is optionally substituted aryloxy or

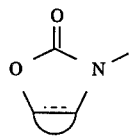

Compounds where A is an aryloxy group are insoluble in water if $Z_1$ or A does not contain a water-solubilising group. This renders them ineffective as gelatin hardeners.

JP 03259243 discloses, as gelatin hardeners, amino phosphorus compounds of the formula:

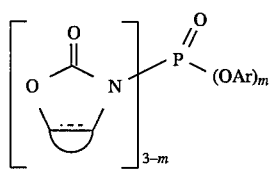

where Ar is optionally substituted aryl; m=1 or 2.

JP 04157453 discloses, as gelatin hardeners, the following amino phosphorus compounds:

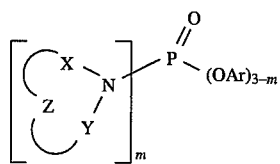

where Ar is optionally substituted aryl; X is CO or $SO_2$; Y is O, S, N(R), or C(R)=N; Z is the atomic grouping required to complete a 5- or 6-membered heterocyclic ring; m=1 or 2.

JP 04157454 discloses similar amino phosphorus compounds:

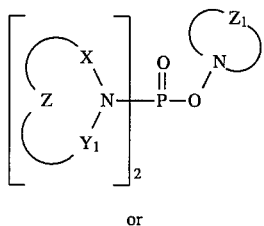

or

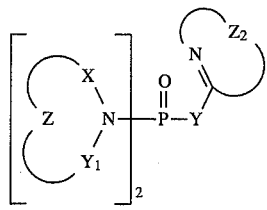

where X is CO or $SO_2$; $Y_1$ is O, S, N(R), or C(R)=N; Y is O or S; Z, $Z_1$ and $Z_2$ are the atomic groupings required to complete 5- or 6-membered heterocyclic rings.

JP 04157455 discloses, as gelatin hardeners, trisubstituted amino phosphorus compounds of the formula:

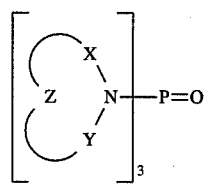

where X is CO or $SO_2$; Y is O, S, N(R), or C(R)=N; Z is the atomic grouping required to complete a 5- or 6-membered heterocyclic ring.

BRIEF DESCRIPTION OF THE INVENTION

The present invention provides an alternative group of phosphorus-containing gelatin hardeners, According to the present invention there is provided, as a gelatin-hardener, a compound of the formula:

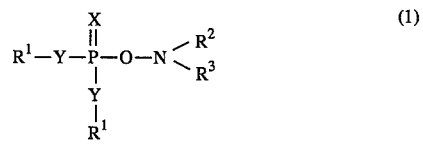

in which:

X represents O, S or is absent, each Y independently represents O, S or a bond, each $R^1$ independently represents an aliphatic group or the two $R^1$ groups together represent the necessary atoms to complete a 5, 6 or 7-member ring and $R^2$ and $R^3$ independently represent hydrogen, a cyclic or acyclic group or $R^2$ and $R^3$ together represent the necessary atoms to complete a heterocyclic ring which may optionally have a ring fused thereto.

The present invention presents an inexpensive, readily prepared, soluble, non-volatile gelatin crosslinking agent which solves the problems of vapour toxicity associated with formaldehyde. In addition, hardening of the gelatin has been shown to be essentially complete within three days of coating, particularly if the film is heated immediately after coating. This results in improved aging performance.

The synthesis of the compounds in the present invention is generally straightforward, and usually one step from commercially available materials.

DESCRIPTION OF PREFERRED EMBODIMENTS

In the compounds of Formula (1) each $R^1$ independently represents an aliphatic group, generally of up to 10 carbon atoms, preferably up to 5 carbon atoms, such as, an alkyl group, an alkenyl group or an alkynyl group, which may be linear or cyclic. Also included are embodiments in which both $R^1$ groups together form an alkylene group of 2, 3 or 4 carbon atoms and hence complete a 5, 6 or 7-membered ring.

In the compound of formula (1) each $R^1$ is preferably an alkyl group of from 1 to 5 carbon atoms.

$R^2$ and $R^3$ may be independently selected from hydrogen, alkyl, preferably containing 1 to 5 carbon atoms, or acyl, preferably containing up to 5 carbon atoms, e.g., acetyl. Alternatively, and most preferably, $R^2$ and $R^3$ together represent the necessary atoms selected from C, N, O and S to complete a saturated heterocyclic ring, e.g., succinimide or an unsaturated heterocyclic ring, e.g., maleimide, 2-pyridone etc.

In the compound of Formula (1), the phosphorus atom may be pentavalent (X=O or S) or tervalent (X is absent). Preferably, X is O or absent.

As is well understood in this technical area, a degree of substitution may be tolerated in $R^1$ to $R^3$. As a means of simplifying the discussion and recitation of these groups, the terms "groups" and "moiety" are used to differentiate between chemical species that allow for substitution or which may be substituted and those which do not or may not be so substituted. For example, the phrase "alkyl group" is intended to include not only pure hydrocarbon alkyl chains, such as methyl, ethyl, octyl, cyclo-hexyl, iso-octyl, tertbutyl and the like, but also alkyl chains bearing conventional substituents known in the art, such as hydroxyl, alkoxy, phenyl, halogen (F, Cl, Br and I), cyano, nitro, amino etc. The phrase "alkyl moiety" or "alkyl" on the other hand is limited to the inclusion of only pure hydrocarbon alkyl chains, such as methyl, ethyl, propyl, cyclohexyl, iso-octyl, t-butyl and the like.

Generally the group $-NR^2 R^3$ contains not more than 12 skeletal atoms.

Examples of compounds useful in this invention include:

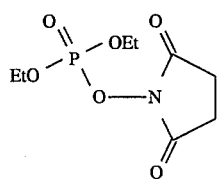

1

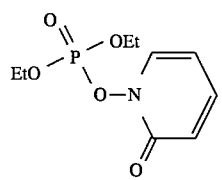

2

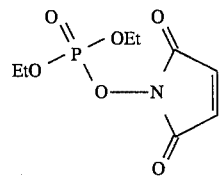

3

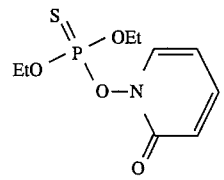

4

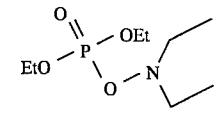

5

-continued

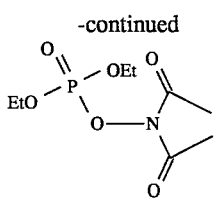

6

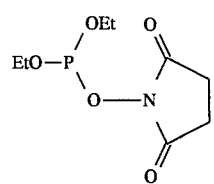

7

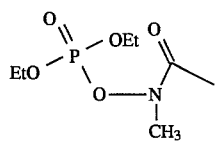

8

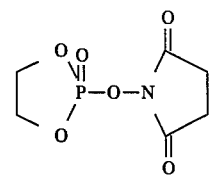

9

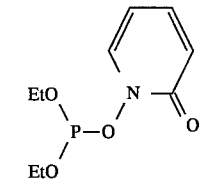

10

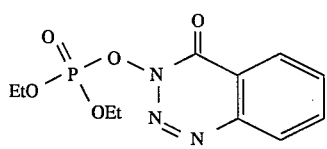

11

Typically, the hardener compounds are incorporated immediately prior to the coating of emulsion or associated gelatin layers. Optimum hardening effect is obtained at substantially neutral pH, e.g., in the range 5 to 7. The hardener compounds are typically added in amounts corresponding to 0.001 mmol to 0.01 mol per gram of gelatin, preferably 0.005 mmol to 0.002 mol per gram of gelatin, most preferably 0.1 mmol to 0.6 mmol per gram of gelatin. The compounds are typically added as a 0.1– 80 w/w % solution in water or a lower alcohol, preferably as a 1–50% solution, most preferably as a 5–30% solution, but may also be added neat. After coating, the film may be stored at 10° to 65° C., preferably at 15° to 50° C., and most preferably at 20° to 45° C. for a period of up to 100 hours, preferably up to 50 hours, and most preferably up to 24 hours.

The hardness of the film may be measured using any of the published techniques. There is no universally accepted measure of film hardness, but a number of empirical tests have been devised which provide an indication of the relative hardness of a film. One such test is the Dornberg test described below.

Dornberg Test Method

A strip of film of suitable dimensions is soaked in the appropriate developer at a known temperature for a known time. The wet film is then subjected to a point force of increasing torque, which gives a measure of the toughness of the film, which in turn is related to the degree of gelatin crosslinking. The apparatus is described in detail below.

A horizontal bar is attached to a motor drive such that the bar travels at constant speed. Affixed to the bar is a pivot placed 160 mm from a stylus, also attached to the bar, on its lower surface. The stylus consists of 0.014 inch diameter 316 gauge stainless steel wire, looped over a 0.1875 inch diameter steel rod. The stylus is arranged to lie parallel to the direction of travel of the bar. A fixed weight, W, is applied to the upper surface of the rod at a distance from the stylus such that at one extreme the weight is 160 mm from the stylus (i.e., directly above the pivot), and at the other extreme the stylus is 40 mm from the weight. The apparatus is thus designed such that at one extreme the force on the film is zero, and at the other extreme the force corresponds to 0.75W.

As the stylus is drawn across the surface of the film strip, it exerts a force on the film that varies linearly from 0 to 0.75W. The minimum force required to produce a visible scratch is quoted as the Dornberg number, and obviously a higher number indicates a greater degree of hardening. For the most accurate and reproducible results, the weight W is selected so that the scratch covers approximately half the available range. Acceptable Dornberg values are generally at least 5, preferably at least 30, and most preferably at least 50.

The degree of hardness required for a photographic element is largely dictated by the amount of physical handling that the film must survive during conversion and use. Therefore, X-ray films, which are used in cartridges and receive less handling, tend to be softer (Dornberg number < 100, often about 40) than graphic art films (Dornberg number much higher, typically >800). Of equal importance, however, is the ability to process the film a short time (e.g. 2 hours) after coating. This is critical for quality control purposes in the factory. Elements of the invention are capable of being processed soon after coating (2 hours).

The hardeners of the invention may be used alone or in combination with other hardeners of the invention or known hardeners.

The photographic materials of the invention may comprise any suitable silver halide based imaging material including: colour papers, colour negative films, colour reversal films (either with or without couplers), photosensitive materials for graphic arts (e.g., lith films), photosensitive materials for use with cathode ray tubes or phosphor screens (e.g., x-ray emulsions), photosensitive materials for laser exposure (e.g., imagesetting films), photosensitive materials for dye transfer processes (inhibition transfer processes), photosensitive materials for colour diffusion transfer processes, photosensitive materials for silver salt diffusion transfer processes, photographic emulsion for silver dye-bleach processes, photosensitive materials for thermal development (i.e., photothermographic materials) and photosensitive materials for physical development.

Another major area of utility is in printing plates of the diffusion transfer type, similar to those sold under the trade mark ONYX by Minnesota Mining and Manufacturing Company. Such materials are described, for example, in U.S. Pat. No. 4,361,635 and comprise an upper layer of nucleating sites for the physical development of a silver image. When processed in a processing solution comprising a silver halide solvent, silver halide in the unexposed areas dissolves in the processing medium, then diffuses to the surface layer where it contacts the nucleating species and precipitates as metallic silver. The resulting silver image can be used for lithographic printing. Effective hardening of the gelatin is crucial to the run-length of plates of this type, but it must not degrade the hydrophilic character of the non-image areas.

All the above materials generally comprise a support having coated thereon one or more layers of photographic silver halide emulsion, and may additionally comprise one or more additional gelatin layers free from silver halide, such as topcoat layers, interlayers, antihalation layers, etc. The hardeners of the invention may be used in any or all of such layers.

The silver halide photographic emulsion may be any of silver bromide, silver iodobromide, silver iodochlorobromide, silver chlorobromide, silver chloride and silver iodochloride.

The silver halide grains in the photographic emulsion may comprise regular crystals of cubic, orthorhombic, tabular, octahedral or tetrahedral habit, or irregular crystals, such as spherical or composite grains.

Each of the silver halide grains may be made up of a uniform phase through its core and surface layer, or it may be dissimilar in phase between the core and the surface. It is also possible to use two or more independently prepared silver halide emulsions as a mixture. In addition, the silver halide particles may be of the surface latent image type or of the internal latent image type. In the former, the latent image is formed on the surface of the grains, and in the latter, the image is formed inside the grains. The surface latent image type of grain is used for negative-type emulsions and the internal latent image type for internal latent image type emulsions and prefogged direct reversal type emulsions.

As regards the average grain size of the silver halide emulsion, for certain applications, notably graphic arts films and printing plates, fine grains, e.g., 1 µm (micrometer) or less, are preferred and very fine grains not larger than 0.5 µm are particularly preferable. While the grain size distribution is optional, a monodispersion is preferable for printing plate and graphic art applications. The term "monodispersion" as used herein means that, whether by in weight or number, at least 95% of grains are sized within ±40% of the mean grain size.

For certain other applications, e.g., X-ray films, a preferred silver halide emulsion comprises laminar grains having a thickness of 0.5 µm or less, preferably 0.3 µm or less, and a diameter of 0.6 µm or greater and in which laminar grains having an average aspect ratio of 5 or more, account for more than 50% of their total projected area.

The silver halide emulsions used in this invention can be prepared according to the processes described, for example, in "Chimie et Physique Photographique" by P. Glafkides (Paul Montel, 1967), "Photographic Emulsion Chemistry" by G. F. Duffin (Focal Press, 1966) and "Making and Coating Photographic Emulsion" by V. L. Zelikman (Focal Press 1964).

When the silver halide grains used in this invention are formed, the growth of grains may be controlled by adding a silver halide solvent, such as ammonia, potassium thiocyanate, ammonium thiocyanate and thioether compounds, as disclosed in U.S. Pat. Nos. 3271157, 3574628, 3704130, 4297439 and 4276374.

The formation or physical ripening of the silver halide crystals may be carried out in the presence of a cadmium salt, a zinc salt, a lead salt, a thallium salt, an iridium salt or complex salt thereof, a rhodium salt or complex salt thereof or a ruthenium salt or complex salt thereof, or mixtures thereof.

The silver halide emulsion may also contain a sensitiser so as to render the emulsion sensitive to any radiation falling within the absorption spectrum of the chosen sensitiser, as described, for example, in Neblette's Handbook of Photography and Reprography pp. 73 to 112 (9th Edition).

Preferred sensitisers include cyanine and merocyanine dyes, the use of which is well known to the person skilled in the art.

The photographic emulsion may also be chemically sensitised. Known methods for chemical sensitisation of silver halide emulsions include sulphur sensitisation, reduction sensitisation and noble metal sensitisation. Chemical sensitisation may be effected by any or a combination of such methods.

The usual method for noble metal sensitisation is gold sensitisation and for this purpose, a gold compound, generally a complex salt of gold, e.g., potassium chloroaurate, auric trichloride etc. is utilized. Complex salts of other noble metals such as platinum, palladium, rhodium etc., may also be used. Sulphur sensitisers include, in addition to sulphur compounds contained in gelatin, various sulphur compounds such as thiosulphates, thiourea compounds, thiazoles and rhodanines e.g., allyl thiocarbonate, thiourea, allyl isothiocyanate, cysteine etc. Examples of such methods are described in U.S. Pat. No. 2,448,060, 2,540,085, 2,597,856, and 2,597,915 and British Patent No. 618961.

Photographic silver halide emulsions useful in the present invention can also be sensitized by other means, such as by alkylene oxide polymers, many of which are well known to those skilled in the photographic art. Typical polyalkylene oxide polymers include those disclosed in U.S. Pat. Nos. 2,423,549 and 2,441,389.

The emulsions may also be chemically sensitized with reducing agents such as stannous salts (U.S. Pat. No. 2,487,050), polyamines such as diethylene triamine (U.S. Pat. No. 2,518,698), polyamines such as spermine (U.S. Pat. No. 2,521,925), or bis-($\beta$-aminoethyl) sulfide and its water-soluble salts (U.S. Pat. No. 2,521,926).

The emulsions of the invention can also contain speed-increasing compounds of the quaternary ammonium type as disclosed in U.S. Pat. Nos. 2,271,623, 2,238,226, 2,334,864, or the thiopolymers disclosed in Canadian Patent Application Nos. 783752 and 783753.

Supersensitisers may also be employed.

The photographic emulsions may be high contrast, e.g., lith films, containing a hydrazine compound or other additives known in the art. Such materials are disclosed, for example, in U.S. Pat. Nos. 2322027, 2419974, 2419975, 4166742, 4168977, 4211857, 4224401, 4743739, 4272606, 4272614, 4311781 and 4323643.

The silver halide emulsion may contain a variety of compounds for the prevention of fog that would otherwise occur during the manufacturing process, preservation or photographic processing and for the stabilisation of photographic performance. Examples of such antifoggants and stabilisers include: azoles, such as benzothiazolium salts, nitroimidazoles, nitroindazoles, triazoles, benzotriazoles, benzimidazoles (particularly the nitro- or halogen-substituted benzimidazoles, e.g., bromobenzimidazoles, chlorobenzimidazoles etc.); heterocyclic mercapto compounds, such as mercaptothiazoles, mercaptobenzothiazoles, mercaptobenzimidazoles, mercaptothiadiazoles, mercaptotetrazoles (particularly 1-phenyl-5-mercaptotetrazole), and mercaptopyrimidines; thioketo compounds (e.g., oxazolinethione); azaindenes, such as triazaindenes, tetraazaindenes (particularly 4-hydroxy-substituted-(1,3,3a,7)-tetraazaindenes); benzenethiosulphonic acids; benzenethiosulphinic acids and benzenesulphonamide. Amongst these compounds, benzotriazoles (e.g., 5-methylbenzo-triazole and nitroindazoles (e.g., 5-nitroindazole) are preferred. These compounds may also be incorporated in the processing solution.

The photographic materials may also contain other inorganic or organic hardening agents in the photographic emulsion layer or other hydrophilic colloid layer. For this purpose chromium salts (chrome alum, chromium acetate etc.), aldehydes (formaldehyde, glyoxal, glutaraldehyde etc.), N-methylol compounds (dimethylolurea, methyloldimethylhydantoin etc.), dioxane derivatives (2,3-dihydroxydioxane etc.), active vinyl compounds (1,3,5-triacryloyl-hexahydro-s-triazines, 1,3-vinyl-sulphonyl-2-propanol etc.), active halogen compounds (2,4-dichloro-6-hydroxy-s-triazine etc.), mucohalogenic acids (mucochloric acid, mucophenoxychloric acid etc.), and the like may be used.

The silver halide emulsion or other hydrophilic colloid layer may also contain a variety of surface active agents for purposes such as the improvement of coating properties, antistatic properties, slip properties, emulsion dispersibility, anti-adhesion properties and photographic properties (e.g., development acceleration, increase in contrast, sensitisation etc.).

Non-ionic surfactants may be employed such as saponin (steroidal), polyethylene glycol, polyethylene glycol/polypropylene glycol condensate, polyethylene glycol alkyl ethers, polyethylene glycol alkyl aryl ethers, polyethylene glycol esters, polyethylene glycol sorbitan esters, polyalkylene glycol alkylamines or alkylamides, silicone polyethylene oxide adducts), glycidol derivatives (e.g., alkenylsuccinic acid polyglyceride, alkylphenol polyglyceride), polyhydric alcohol-fatty acid esters, sugar alkyl esters etc.

Anionic surfactants containing acid groups, such as a carboxyl group, a sulpho group, a phospho group, a sulphuric acid ester group, a phosphoric acid ester group etc., for example, alkylcarboxylate, alkylsulphonates, alkylbenzenesulphonates, alkylnaphthalenesulphonates, alkylsulphuric acid esters, alkylphosphoric acid esters, n-acyl-n-alkyltaurines, sulphosuccinic acid esters, sulphoalkylpolyoxyethylene alkylphenyl ether, polyoxyethylene alkylphosphoric acid esters etc., may also be used.

Amphoteric surfactants such as amino acids, aminoalkylsulphonic acids, aminoalkylsulphuric or phosphoric acid esters, alkylbetaines, amine oxides etc.; and cationic surfactants, such as alkylamines, aliphatic or aromatic quaternary ammonium salts, heterocyclic quaternary ammonium salts, such as pyridinium salts, imidazolium salts etc., aliphatic or heterocyclic ring-containing phosphonium or sulphonium salts etc. may be used.

The phetographic emulsion layer and/or the hydrophilic colloid layer may also include a matting agent, such as silica, magnesium oxide, polymethyl methacrylate etc., for the purpose of preventing adhesion.

The silver halide emulsion may contain a discolouration prevention agent, colour-fog preventing agent, UV light absorber, and other additives. Detailed description of these additives will be found in Research Disclosure Vol. 176 (1978, XII) RD-17643.

In certain embodiments, the emulsion or an associated layer may contain one or more developing agents for silver halide (or their precursors), as described, for example, in Research Disclosure No. 17364 (September 1978), Canadian Patent No. 766,708 and European Patent Application No. 0,532,192. This enables activation processing in alkaline solutions that are essentially free from conventional developers.

The finished emulsion and any associated layers are applied to a support which may be made of an opaque material, such as baryta paper, resin-coated paper, synthetic paper or a transparent material, such as glass or a plastics film, e.g., cellulose triacetate; cellulose diacetate, nitrocellulose, polystyrene, polyethylene terephthalate (polyester) etc.

The photographic material of the invention can be exposed using conventional sources, such as natural light (sunlight), tungsten lamps, fluorescent lamps, mercury lamps, xenon arc lamps, carbon arc lamps, xenon flash lamps and CRT spots. The exposure time is not limited to that for ordinary cameras (1/1000 sec to 1 sec) and exposures as short as $1/10^4$ to $1/10^7$ seconds by a xenon flash lamp or laser scanner are also possible. Exposures longer than 1 second are also possible. If necessary, it is possible to control the spectral energy distribution of the light for exposure by means of a proper colour filter. The light-sensitive material of the invention can be exposed with laser light or light emitted by the fluorescent material excited by electron ray, X-ray, γ-ray, or α-ray.

The light-sensitive material of the invention may be processed by any known method with any known processing solution, such as those disclosed in Research Disclosure No. 176, pp. 28-30 (RD-17643). Thus, for example, dihydroxybenzenes (e.g., hydroquinone), 3-pyrazolidones (e.g., 1-phenyl-3-pyrazolidone and 4,4-dimethyl-1-phenyl-3-pyrazolidone), aminophenols (e.g., 4-methylaminophenol) etc., can be used alone or in combination.

This invention will now be described with reference to the following Examples.

EXAMPLE 1 a) Synthesis of Compound 1

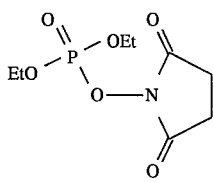

A solution of N-hydroxysuccinimide (25.2 g, 0.219 mol) in dry THF (400 ml) was treated with triethylamine (28.8 ml), whereupon a colourless precipitate formed. Diethyl chlorophosphate (30 ml, 0.20 mol) was added dropwise and the mixture was heated to reflux for 16 hrs, resulting in the formation of a thick white precipitate. After this time no chlorophosphate was present as shown by $^{31}$p NMR of the crude reaction mixture. The mixture was allowed to cool, and was then filtered and the filtrates were evaporated to leave an oil. This oil was dissolved in ethyl acetate (200 ml), the resulting solution being washed with saturated aqueous sodium bicarbonate solution (50 ml) and water (100 ml). The aqueous wash was backextracted with ethyl acetate (100 ml), the combined ethyl acetate extracts being dried over magnesium sulphate. The magnesium sulphate was removed by filtration, and the combined filtrates were evaporated to leave a colourless oil. The last traces of ethyl acetate were removed from this oil by azeotroping with dichloromethane, to leave the product as a colourless oil (46.0 g, 92%).

b) Evaluation of Compound 1 in a Fine-Grained Silver Chlorobromide Emulsion

A fine-grained 0.09 micron, 96% silver chlorobromide emulsion with rhodium doping was prepared and chemically sensitized using a thiosulphate and gold digestion using methods known to those skilled in the art. Samples of this emulsion were coated on to a polyester base material such that the silver coverage was 2.5 $gm^{-2}$ the total gelatin coverage was 3.6 $gm^{-2}$ and the hardener, which was added as a 10% solution in methanol, was added at the levels listed in the following Table. Hardness values were determined after 2 hours at room temperature by the Dornberg method.

| Hardener mmol/g gel | Dornberg Number |
|---|---|
| 0.13 | 30 |
| 0.18 | 51 |
| 0.23 | 60 |
| 0.12 | 260* |

*measured after heating at 38° C. for 16 hours

Thus Compound 1 shows good hardening activity in this emulsion.

c) Effect of Compound 1 on Sensitometric Parameters

Coatings of a fine-grained emulsion, prepared as described above, were exposed on a UV Contacting exposing frame through a 0–2.6 continuous tone wedge and processed through 3M RDC V Rapid Access chemistry. The sensitometric parameters for coatings containing Compound 1, and a control hardened with formaldehyde, are shown in the following Table.

| | Hardener mmol/g gel | Dmin | Dmax | SP-1* | Con1** |
|---|---|---|---|---|---|
| Cpd1 | 0.13 | 0.04 | 4.62 | 1.82 | 15.26 |
| HCHO | 0.34 | 0.06 | 4.59 | 1.77 | 16.71 |

*speed at density 0.1 above fog
**contrast between densities 0.1 and 2.5 above fog d) Evaluation of Compound 1 in a Scanner Emulsion A 0.25 micron cubic chlorobromide emulsion (64% AgCl) was prepared by a conventional double-jet precipitation method familiar to those skilled in the art. The emulsion was doped with iridium and ruthenium metal ions to provide good reciprocity behaviour, and was chemically sensitised with sodium thiosulphate and sodium tetrachloroaurate. The resulting grains were spectrally sensitised at 488 nm using a dye suitable for argon ion laser sensitisation (Dye D). The emulsion was coated on to a clear polyester base material at the following nominal coverages:

| Silver | 3.9 $gm^{-2}$, |
|---|---|
| Gelatin | 3.1 $gm^{-2}$, | using Compound 1 as the gelatin crosslinking agent. The hardness values as determined by the Dornberg method for coatings of a scanner emulsion containing Compound 1 as the hardening agent, 2 hours at room temperature after coating are reported in the following Table.

| Hardener mmol/g gel | Dornberg Number |
|---|---|
| 0.14 | 25 |
| 0.23 | 48 |
| 0.33 | 89 | e) Effect of Compound 1 on Sensitometric Parameters

This example demonstrates that incorporation of Compound 1 into this scanner emulsion has no detrimental effect on sensitometric parameters.

Coatings of a scanner emulsion, prepared as described above, were exposed by a single Xenon flash through a 490 nm narrow band cutoff filter and a 0–4.0 continuous tone wedge, and processed through 3M RDC V Rapid Access chemistry. The sensitometric parameters for coatings containing Compound 1, as well as a reference sample crosslinked with formaldehyde, reported in the following Table.

| Hardening Agent | Amount mmol/g gel | Dmin | Dmax | SP-1 | Con1 |
|---|---|---|---|---|---|
| HCHO (Comparison) | 0.63 | 0.09 | 4.27 | 2.81 | 2.75 |
| 1 (Invention) | 0.14 | 0.10 | 4.32 | 2.60 | 3.71 |
|  | 0.23 | 0.07 | 4.27 | 2.50 | 4.25 |
|  | 0.33 | 0.05 | 4.27 | 2.48 | 4.11 | f) Effect of Heat on the Hardening Activity of Compound 1

Coatings of the same scanner emulsion above were heated at 38° C. for 16 hours after coating, and then their hardness values were determined using the Dornberg method. The results reported in the following Table indicate very effective hardening by Compound 1 under these conditions.

| Hardener mmol/g gel | Dornberg Number |
|---|---|
| 0.14 | 220 |
| 0.23 | 360 |
| 0.33 | >800 | g) Evaluation of Compound 1 in a X-Ray Emulsion

A pure silver bromide laminar emulsion of mean aspect ratio 8:1, and mean grain diameter 1.5 micron was prepared by a double-jet precipitation procedure familiar to those skilled in the art, as described in U.S. Pat. No. 5028521. The resulting emulsion was chemically sensitised with gold thiocyanate and spectrally sensitised to 545 nm, as described in U.S. Pat. No. 5028521. Samples of this emulsion were coated on to a polyester base material such that the silver coverage was 2.0 $gm^{-2}$, the gelatin coverage was 1.30 $gm^{-2}$, and the hardener levels were as listed in the following Table.

The hardness values were determined after 48 hours at 38° C. as by the Dornberg method.

| Hardener mmol/g gel | Dornberg Number |
|---|---|
| 0.14 | 17 |
| 0.28 | 28 |
| 0.35 | 31 | h) Effect of Compound 1 on Sensitometric Parameters

This example demonstrates that incorporation of Compound 1 into this X-ray emulsion has no detrimental effect on sensitometric parameters.

Coatings of the X-ray emulsion containing gelatin crosslinked with Compound 1 were exposed by a tungsten filament lamp through a Wrattan 58 filter and 0–4 continuous tone density wedge for 0.1 sec. The samples were then developed in 3M XAD3(TM) chemistry for 25 sec at 34° C., fixed, washed and dried. As a reference material the same coatings containing gelatin crosslinked with bis(vinylsulphonyl)propan-2-ol were handled in the same way. The results are reported in the following Table.

| Hardening Agent | Amount mmol/g gel | Dmin | Dmax | SP-1 | Con-A* |
|---|---|---|---|---|---|
| 1,3-bis(vinyl-sulphonyl) propan-2-ol (comparison) | 0.14 | 0.19 | 2.20 | 2.30 | 1.19 |
| 1 (Invention) | 0.35 | 0.24 | 2.04 | 2.22 | 1.10 |

*contrast between 0.13 and 1.0 above fog i) Effect of Compound 1 on Antihalation Dyes

This example demonstrates that incorporation of Compound 1 into a pan-chromatic antihalation layer does not cause significant bleaching of the antihalation dyes.

Three different antihalation dyes A, B and c, with the following structures, were coated such that the gelatin coverage was 2.52 $gm^{-2}$, of which 0.94 $gm^{-2}$ was in the topcoat. The Dornberg number and dye extinctions for coatings containing varying amounts of compound 1 are reported in the following Table.

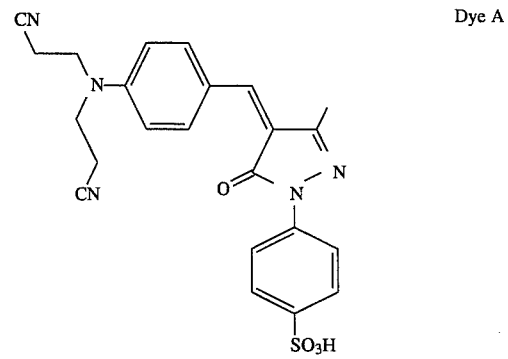

Dye A

-continued

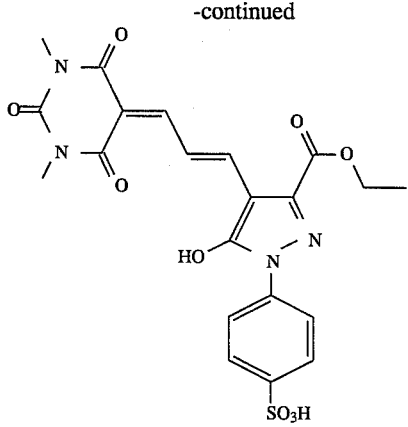

Dye B

Dye C

| Amount of compound 1 mmol/g gel | | | | Extinction/D | | |
|---|---|---|---|---|---|---|
| Topcoat | With dyes | Total | Dornberg Number | A 440 nm | B 490 nm | C 595 nm |
| 0.08 | 0.30 | 0.38 | 49 | 0.687 | 0.786 | 0.711 |
| 0.16 | 0.30 | 0.46 | 55 | 0.647 | 0.746 | 0.682 |
| 0.32 | 0.30 | 0.62 | 56 | 0.617 | 0.706 | 0.647 |

There is only a small difference in values of the dye extinctions with excess of hardener. Of significance is the observation that the hardening activity is not affected by the presence of the dyes.

EXAMPLE 2

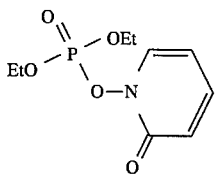

A) Synthesis of Compound 2

A solution of N-hydroxy-2-pyridone (11.53 g; 0.104 mol) in dry dichloromethane (200 ml) was treated with triethylamine (14.5 ml, 0.104 mol), followed by diethyl chlorophosphate (10 ml, 69.2 mmol). The mixture was stirred at room temperature for 2 days. After this time no chlorophosphate was present as shown by $^{31}p$ NMR of the crude reaction mixture. The mixture was diluted with dichloromethane (200 ml) and then poured into water (200 ml). The dichloromethane phase was separated, the resulting solution being washed with saturated aqueous sodium bicarbonate solution (50 ml) before being dried over magnesium sulphate. The magnesium sulphate was removed by filtration, and the combined filtrates were evaporated to leave the product as a yellow oil (15.42 g, 90%).

b) Evaluation of Compound 2 in a Fine-Grained Silver Chlorobromide Emulsion

A fine-grained 0.09 micron, 96% silver chlorobromide emulsion with rhodium doping was prepared and chemically sensitized using a thiosulphate and gold digestion using methods known to those skilled in the art. Samples of this emulsion were coated with a topcoat onto a polyester base material such that the silver coverage was 2.5 $gm^{-2}$, the total gelatin coverage was 3.8 $gm^{-2}$, and the hardener levels used and hardness values, which were determined by the Dornberg method both at room temperature 1 hour after coating and after heating at 38° C. for 16 hours, are reported in the following Table.

| Hardener | Dornberg Number | |
|---|---|---|
| mmol/g gel | RT/1 hr | 38° C./16 hr |
| 0.10 | 52 | 85 |
| 0.30 | 195 | 220 |

Thus Compound 2 shows good hardening activity in this emulsion.

c) Effect of Compound 2 on Sensitometric Parameters

This example demonstrates that incorporation of Compound 2 into the above fine-grained photographic emulsion has no detrimental effect on sensitometric parameters.

Coatings of a fine-grained emulsion, prepared as described above, were exposed on a UV Contacting exposing frame through a 0–2.6 continuous tone wedge, and processed through 3M RDC V Rapid Access chemistry. The sensitometric parameters for coatings containing Compound 2, as well as a reference sample crosslinked with formaldehyde, after 16 hours at 38° C. are reported in the following Table.

| Hardening Agent | Amount mmol/g gel | Dmin | Dmax | SP-1 | Con1 |
|---|---|---|---|---|---|
| HCHO (Comparison) | 0.31 | 0.03 | 4.83 | 1.40 | 8.5 |
| 2 (Invention) | 0.10 | 0.06 | 5.01 | 1.46 | 9.2 |
| | 0.20 | 0.04 | 4.67 | 1.41 | 9.2 |
| | 0.30 | 0.04 | 4.58 | 1.40 | 9.2 |

EXAMPLE 3 a) Synthesis of Compound 3

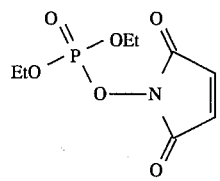

A solution of N-hydroxymaleimide (5.0 g, 44.2 mmol) in dry dichloromethane (100 ml) was treated with triethylamine (6.2 ml, 44.2 mmol) to form a dark red-brown solution. This was treated with diethyl chlorophosphate (5.8 ml, 40.2 mmol) and the mixture was stirred at room temperature overnight. After this time no chlorophosphate was present as shown by $^{31}$p NMR of the crude reaction mixture. The mixture was diluted with dichloromethane (200 ml) and then poured into water (100 ml). The dichloromethane phase was separated, the resulting solution being washed with saturated aqueous sodium bicarbonate solution (50 ml) before being dried over magnesium sulphate. The magnesium sulphate was removed by filtration, and the combined filtrates were evaporated to leave a dark brown oil. The mixture was purified by column chromatography using diethyl ether as eluent to give the product as a pale yellow oil (6.68 g, 67%).

b) Evaluation of Compound 3 in a Fine-Grained Silver Chlorobromide Emulsion

A fine-grained 0.09 micron, 96% silver chlorobromide emulsion with rhodium doping was prepared and chemically sensitized using a thiosulphate and gold digestion using methods known to those skilled in the art. Samples of this emulsion were coated with a topcoat on to a polyester base material such that the silver coverage was 2.5 gm$^{-2}$, the gelatin coverage was 3 8 gm$^{-2}$, and the hardener levels used and the obtained hardness values, which were determined by the Dornberg method both at room temperature 1 hour after coating and after heating at 38° C. for 16 hours, are reported in the following Table.

| Hardener | Dornberg Number | |
|---|---|---|
| mmol/g gel | RT/1 hr | 38° C./16 hr |
| 0.10 | 17 | 160 |
| 0.20 | 22 | 210 |
| 0.30 | 25 | 180 |

Thus, Compound 3 shows good hardening activity.

c) Effect of Compound 3 on Sensitometric Parameters

This Example demonstrates that incorporation of Compound 3 into the above fine-grained photographic emulsion has no detrimental effect on sensitometric parameters.

Coatings of a fine-grained emulsion, prepared as described above, were exposed on a UV Contacting exposing frame through a 0–2.6 continuous tone wedge, and processed through 3M RDC V Rapid Access chemistry. The sensitometric parameters for coatings containing Compound 3, as well as a reference sample crosslinked with formaldehyde, after 16 hours at 38° C. are reported in the following Table.

| Hardening Agent | Amount mmol/g gel | Dmin | Dmax | SP-1 | Con1 |
|---|---|---|---|---|---|
| HCHO (Comparison) | 0.31 | 0.03 | 4.83 | 1.40 | 8.5 |
| 3 (Invention) | 0.10 | 0.04 | 4.98 | 1.40 | 9.3 |
| | 0.20 | 0.03 | 4.50 | 1.38 | 9.5 |
| | 0.30 | 0.03 | 4.12 | 1.39 | 9.0 | d) Evaluation of Compound 3 in a Scanner Emulsion

A 0.25 micron cubic chlorobromide emulsion (64% AgCl) was prepared by a conventional double-jet precipitation method familiar to those skilled in the art. The emulsion was doped with iridium and ruthenium metal ions to provide good reciprocity behaviour, and was chemically sensitised with sodium thiosulphate and sodium tetrachloroaurate. The resulting grains were spectrally sensitised at 488 nm using a dye suitable for argon ion laser sensitisation (Dye D). The emulsion was coated with a topcoat on to a clear polyester base material at the following total coverages:

| Silver | 4.0 gm$^{-2}$, |
|---|---|
| Gelatin | 4.0 gm$^{-2}$, | using compound 3 as the gelatin crosslinking agent. Hardness values were determined by the Dornberg method both after 1 hour at room temperature and after 16 hours at 38° C. and are reported in the following Table.

| Hardener | Dornberg Number | |
|---|---|---|
| mmol/g gel | RT/1 hr | 38° C./16 hr |
| 0.10 | 5 | 85 |
| 0.20 | 25 | 125 |
| 0.30 | 25 | 140 | e) Effect of Compound 3 on Sensitometric Parameters

This Example demonstrates that incorporation of Compound 3 into the above scanner emulsion has no significant detrimental effect on sensitometric parameters.

Coatings of a scanner emulsion, prepared as described above, were exposed by a single Xenon flash through a 490 nm narrow band cutoff filter and a 0–4.0 continuous tone wedge, and processed through 3M RDC V Rapid Access chemistry. The sensitometric parameters for coatings containing Compound 3, as well as a reference sample crosslinked with formaldehyde, after 16 hours at 38° C. are reported in the following Table.

| Hardening Agent | Amount mmol/g gel | delta Dmin* | Dmax | SP-1 | Con1 |
|---|---|---|---|---|---|
| HCHO (Comparison) | 0.55 | 0.00 | 5.00 | 2.98 | 3.2 |
| 3 (Invention) | 0.10 | 0.08 | 5.00 | 3.16 | 3.4 |
| | 0.20 | 0.03 | 5.01 | 3.12 | 3.3 |
| | 0.30 | 0.15 | 4.83 | 3.14 | 3.2 |

-continued

| Hardening Agent | Amount mmol/g gel | delta Dmin* | Dmax | SP-1 | Con1 |
|---|---|---|---|---|---|

*delta dmin = observed Dmin − Dmin (HCHO)

EXAMPLE 4 a) Synthesis of Compound 4

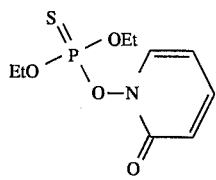

A solution of N-hydroxy-2-pyridone (4.0 g, 36 mmol) in dry dichloromethane (36 ml) was treated with triethylamine (5 ml, 36 mmol), which was added over 5 minutes. This was treated with a solution of diethyl chlorothiophosphate (3.8 ml, 24 mmol) in dichloromethane (4 ml), the residues being washed in with dichloromethane (8 ml), and the mixture was stirred at room temperature overnight. The mixture was diluted with dichloromethane (100 ml) and then poured into water (100 ml). The dichloromethane phase was separated, the resulting solution being dried over magnesium sulphate. The magnesium sulphate was removed by filtration, and the combined filtrates were evaporated to leave the product as a light brown oil (5.85 g, 93%).

b) Evaluation of Compound 4 in a Fine-Grained Silver Chlorobromide Emulsion

A fine-grained 0.09 micron, 96% silver chlorobromide emulsion with rhodium doping was prepared and chemically sensitized using a thiosulphate and gold digestion using methods known to those skilled in the art. Samples of this emulsion were coated on to a polyester base material and the hardener levels and hardness values were determined after 16 hours at 38° C. by the Dornberg method are reported in the following Table.

| Hardener mmol/g gel | Dornberg Number |
|---|---|
| 0.10 | <5 |
| 0.20 | 18 |

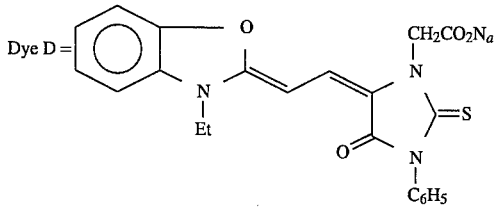

(U.S. Pat. No. 4,336,323)

EXAMPLE 5

This example demonstrates the utility of the hardeners of the invention in a diffusion transfer printing plate.

A lithographic plate construction of the type disclosed in U.S. Pat. No. 4, 361,635 was prepared as follows:

Antihalation Layer

A 100 micron thick polyester film having a photographic subbing coating on one side to increase adhesion of the photographic layers to the base, was coated with a conventional anti-halation layer consisting of gelatin, silica of 5 micron average grain diameter, carbon black, an anionic surface active agent, hydroquinone and compound (I) as hardener. This composition was coated at 2.9g gelatin per square metre. Compound (I) was used at the level of 0.45 m.mol per gram of gelatin, and with the pH adjusted to 5.8.

Photographic Emulsion Layer

A conventional negative-acting cubic, monodispersed silver chlorobromide photographic emulsion containing 64 molar percent silver chloride and 36 molar percent silver bromide with an average grain size of 0.25 microns was prepared by double jetting the silver and halide solutions under controlled pAg. The emulsion was digested with a sulphur sensitiser and sodium tetrachloro-aurate, then sensitised with a conventional red sensitising dye suitable for He—Ne laser address. The pH was adjusted to 5.8 and Compound (I) added at the level of 2.52 m.mol per gram of gelatin before coating the emulsion on top of the antihalation layer at a silver coating weight of $0.7g/m^2$.

Receptor Layer

A receptor layer comprising colloidal palladium, Triton X-100 and dialdehyde starch was coated over the photographic emulsion layers to give a palladium metal coating weight of about 1.4 milligrams per square metre. (Triton X-100 is a surfactant available from Rohm & Haas).

Identical samples were stored at room temperature and 38° for 18 hours, and gave Dornberg hardness values of 56 and 50 respectively after immersion in Onyx (TM) developer (available from 3M).

Similar samples were imagewise exposed, processed in Onyx (TM) developer and mounted on an Apollo 21 web press. Both inked up well, and ran cleanly for at least 30,000 impressions.

EXAMPLE 6

Diffusion transfer printing plates were prepared by the method of Example 5 except that the antihalation layer additionally contained an acrylic latex. Specifically, 20g of a 40% solids by weight dispersion of a butylacrylate/acrylonitrile/methacrylic acid terpolymer (prepared by emulsion polymerisation of the monomers in the weight ratio 54:43:3) was added to 245 g of the coating composition described in Example 5. Two sets of samples were prepared. In samples A, the emulsion was coated at pH 5.8 exactly as described in Example 5, while in samples B the pH was adjusted to 3.5 prior to coating. Both sets were topcoated with the receptor layer of Example 5.

After storage at room temperature for 18 hours, then immersion in Onyx(TM) developer, samples A gave a Dornberg hardness value of 66 and samples B a value of 30. For similar storage at 38° C., the corresponding values were 74 and 46. Despite their lower Dornberg hardness, samples B ran equally well as samples A on press, printing 30,000 impressions cleanly without sign of wear.

For reasons of stability, especially when developing agents are incorporated in the plate coating, it is preferable to coat the emulsions of diffusion transfer plates at an acidic pH. This Example shows that the hardeners of the invention can be used successfully under these conditions.

EXAMPLE 7

(a) Synthesis of Compound 7

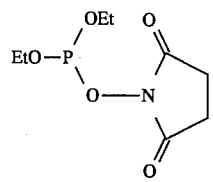

A solution of N-hydroxysuccinimide (17.5 g, 0.152 mol) in dry THF (350 ml) under nitrogen was treated with triethylamine (21.2 ml), whereupon a colourless precipitate formed. Diethyl chlorophosphite (21 ml, 0.145 mol) was added dropwise and the mixture was heated to reflux for 16 hrs, resulting in the formation of a thick precipitate. The mixture was allowed to cool, and was then filtered and the filtrates were evaporated to leave an oil. This oil was dissolved in chloroform (300 ml), and was washed with saturated aqueous sodium bicarbonate solution (100 ml), the aqueous phase being back-extracted with chloroform (3×100 ml). The combined chloroform extracts were dried over magnesium sulphate which was subsequently removed by filtration, and the filtrates were evaporated to leave the product as a golden brown oil (33.0 g, 97%).

(b) Evaluation of Compound 7 in a Scanner Emulsion

A 0.25um cubic chlorobromide emulsion (64% AgCl) was prepared by a conventional double-jet precipitation as in Example 1(d). The emulsion was coated on to a clear polyester base material at the following nominal coverages:

| Silver | 4.00 g/m² |
|---|---|
| Gelatin | 4.26 g/m² | using Compound 7 as the gelatin crosslinking agent. The hardness values as determined by the Dornberg method immediately after coating, and after various periods of incubation at ambient temperature and at 38° C., are given in the Tables below.

| Hardener | Dornberg number at time after coating | | | |
|---|---|---|---|---|
| mmol/g gel | 3 h | 6 h | 21 h | 72 h |
| 0.15 | 6 | 20 | 52 | 105 |
| 0.25 | 27 | 37 | 125 | 185 |
| 0.35 | 85 | 125 | 250 | 270 |
| 0.45 | 112 | 145 | 250 | 310 |
| 0.55 | 112 | 150 | 290 | 300 |

| Hardener | Dornberg number with 38° C. incubation time | | | | |
|---|---|---|---|---|---|
| mmol/g gel | 1.5 h | 3 h | 7 h | 18 h | 72 h |
| 0.15 | 56 | 67 | 140 | 200 | 200 |
| 0.25 | 125 | 155 | 275 | 320 | 330 |
| 0.35 | 260 | 290 | 360 | 380 | 400 |
| 0.45 | 250 | 285 | 350 | 400 | 400 |
| 0.55 | 280 | 320 | 390 | 400 | 390 |

Coatings of the above materials were exposed by a single Xenon flash through a 490nm narrow band cutoff filter and a 0–4.0 continuous tone wedge, and processed through 3M Rapid Access chemistry. The sensitometric properties for coatings containing Compound 7, with HCHO as a reference, are reported in the following Table:

| Hardening Agent | Hardener mmol/g gel | Dmin | Dmax | SP-1 | Con1 |
|---|---|---|---|---|---|
| HCHO | 0.41 | 0.03 | 5.04 | 2.52 | 4.01 |
| Compound 7 | 0.15 | 0.03 | 4.99 | 2.58 | 4.31 |
| " | 0.25 | 0.03 | 4.99 | 2.58 | 4.22 |
| " | 0.35 | 0.12 | 4.87 | 2.81 | 3.51 |
| " | 0.45 | 0.05 | 4.99 | 2.71 | 3.62 |
| " | 0.55 | 0.04 | 4.99 | 2.70 | 3.59 |

(c) Evaluation of Compound 7 in a X-Ray Emulsion

A pure silver bromide laminar emulsion with a mean aspect ratio of 8:1 and mean grain diameter 1.5 μm was prepared as in Example 1(g). Samples of this emulsion were coated onto polyester base such that the silver coverage was 2.0 g/m², the gelatin coverage was 2.15 g/m², with the levels of Compound 7 hardener as listed in the following Table. The hardness values were determined by the Dornberg method immediately after coating, then after incubation for 16 hours both at ambient temperature and at 38° C. A comparison was made with a sample which was crosslinked with a bis(vinylsulphone).

| Hardener | Dornberg number | | |
|---|---|---|---|
| mmol/g gel | after coating | 16 hours at RT | 16 hours at 38° C. |
| 0.041 | <5 | <5 | <5 |
| 0.043 | " | " | 23 |
| 0.077 | " | " | 19 |
| 0.107 | " | " | 32 |
| 0.132 | " | 7.5 | 27 |
| 0.132 | " | 12 | 30 |
| 0.132 | " | 17 | 30 |
| 0.187 | " | 15 | 50 |
| 0.220 | " | 19 | 56 |
| Comparison | <5 | 23 | 44 |

EXAMPLE 8

Compound 10 was prepared from N-hydroxy-2-pyridone and diethylchlorophosphite in the same manner as Compound 7.

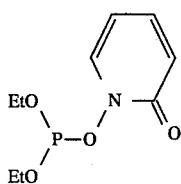

(a) Evaluation of Compound 10 in a Scanner Emulsion

A 0.25 μm cubic chlorobromide emulsion (64% AgCl) was prepared by a conventional double-jet precipitation (as Example 1d). The emulsion was coated on to a clear polyester base material at the following nominal coverages:

| Silver | 4.00 g/m² |
|---|---|
| Gelatin | 4.26 g/m² | using Compound 10 as the gelatin crosslinking agent. The hardness values as determined by the Dornberg method after incubation for a period of 16 hours at 38° C. are given in the Table below.

| Hardener mmol/g gel | Dornberg number |
|---|---|
| 0.20 | 8 |
| 0.35 | 11 |
| 0.50 | 36 |

Coatings of the above materials were exposed by a single Xenon flash through a 490nm narrow band cutoff filter and a 0–4.0 continuous tone wedge, and processed through 3M Rapid Access chemistry. The sensitometric properties for coatings containing Compound 10, with HCHO as a reference, are reported in the following Table:

| Hardening Agent | Hardener mmol/g gel | Dmin | Dmax | SP-1 | ConI |
|---|---|---|---|---|---|
| HCHO | 0.41 | 0.03 | 4.88 | 2.28 | 4.83 |
| Compound 10 | 0.20 | 0.03 | 4.85 | 2.70 | 3.76 |
| " | 0.35 | 0.04 | 4.74 | 2.78 | 3.76 |
| " | 0.50 | 0.07 | 4.34 | 2.96 | 3.35 |

EXAMPLE 9

Compound 11 was prepared in analogous manner to Compounds 1 to 3.

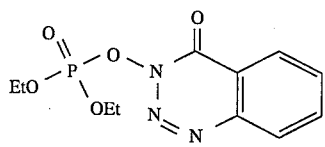

(a) Evaluation of Compound 11 in a Scanner Emulsion

A 0.25 μm cubic chlorobromide emulsion (64% AgCl) was prepared and coated as Example 1 (d), but Compound 11 was used as the gelatin crosslinking agent. The hardness values as determined by the Dornberg method immediately after coating, and after a period of incubation of 16 hours at 38° C., are given in the Table below.

| Hardener mmol/g gel | Dornberg number after coating | Dornberg number after incubation |
|---|---|---|
| 0.20 | 61 | 66 |
| 0.35 | 89 | 90 |
| 0.50 | 102 | 120 |

Coatings of the above materials were exposed by a single Xenon flash through a 490nm narrow band cutoff filter and a 0–4.0 continuous tone wedge, and processed through 3M Rapid Access chemistry. The sensitometric properties for coatings containing Compound 11 with HCHO as a reference, are reported in the following Table:

| Hardening Agent | Hardener mmol/g gel | Dmin | Dmax | SP-1 | ConI |
|---|---|---|---|---|---|
| HCHO | 0.41 | 0.03 | 4.73 | 2.42 | 4.21 |
| Compound 11 | 0.20 | 0.03 | 4.26 | 2.40 | 4.68 |
| " | 0.35 | 0.04 | 4.55 | 2.34 | 4.87 |
| " | 0.50 | 0.07 | 2.97 | 2.30 | 3.80 |

EXAMPLE 10

Compound 8 was prepared by reaction of N-hydroxy-N-methylacetamide with diethylchlorophosphate.

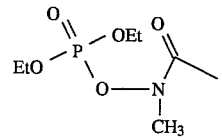

(a) Evaluation of Compound 8 in a Scanner Emulsion

A 0.25 μm cubic chlorobromide emulsion (64% AgCl) was prepared and coated as Example 1 (d), but Compound 8 was used as the gelatin crosslinking agent. The hardness values as determined by the bornberg method after a period of incubation of 16 hours at 38° C. are given in the Table below.

| Hardener mmol/g gel | Dornberg number |
|---|---|
| 0.20 | <0 |
| 0.35 | 0 |
| 0.50 | 8 |

Although less effective than its cyclic analogues, Compound 8 showed some hardening activity.

We claim:

1. A process for hardening gelatin comprising adding a compound of the formula

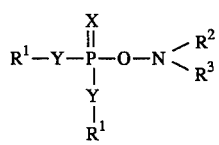

(1)

wherein:

X is a member selected from the group consisting of O and S or X is absent, each Y independently is a member selected from the group consisting of O, S, and a bond between $R^1$ and P, each $R^1$ independently represents an aliphatic group of up to 10 atoms or the two $R^1$ groups together represent the necessary atoms to complete a 5, 6, or 7-membered ring, $R^2$ and $R^3$ are independently members of the group consisting of hydrogen, cyclic groups and acyclic groups or R2 and R3 together represent the atoms necessary to complete a heterocyclic ring, and reacting said compound with gelatin to crosslink said gelatin.

2. The process according to claim 1 wherein $R^1$ represents an alkyl group of 1 to 5 carbon atoms.

3. The process according to claim 2 wherein Y is O.

4. The process according to claim 1 wherein $R^2$ and $R^3$ are members selected from the group consisting of hydrogen, alkyl of 1 to 5 carbon atoms and acyl.

5. The process according to claim 1 wherein —$NR^2R^3$ is a member selected from the group consisting of succinimide, maleimide and 2-pyridone.

6. A method of hardening gelatin which comprises contacting gelatin with a compound of the formula:

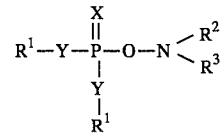

(1)

wherein:

X is a member selected from the group consisting of O and S or X is absent, each Y independently is a member selected from the group consisting of O, S and a bond between $R^1$ and P, each $R^1$ independently represents an aliphatic group of up to 10 atoms or the two $R^1$ groups together represent the necessary atoms to complete a 5, 6 or 7-membered ring, $R^2$ and $R^3$ are independently members of the group consisting of hydrogen, cyclic groups and acyclic groups or $R^2$ and $R^3$ together represent the necessary atoms to complete a heterocyclic ring.

7. The method according to claim 6 wherein $R^1$ represents an alkyl group of 1 to 5 carbon atoms.

8. The method according to claim 7 wherein Y is O.

9. The method according to claim 6 wherein $R^2$ and $R^3$ are members selected from the group consisting of hydrogen, alkyl of 1 to 5 carbon atoms and acyl.

10. The method according to claim 6 wherein —$NR^2R^3$ is a member selected from the group consisting of succinimide, maleimide and 2-pyridone.

11. The method according to claim 6 wherein the gelatin is incorporated in a photographic silver halide emulsion composition.

12. The method according to claim 11 wherein the compound of formula (1) is incorporated at a level of 0.1 mmol/mol Ag to 1 mol/mol Ag.

13. The method according to claim 12 wherein the compound of formula (1) is incorporated at a level of 10 mmol/mol Ag to 60 mmol/mol Ag.

14. The method according to claim 6 to wherein the compound of formula (1) is incorporated as a 0.1 to 80 w/w% solution in water or alcohol.

15. A photographic element comprising a silver halide emulsion layer and a gelatin layer containing photosensitive silver halide, said layer being hardened with a compound of formula:

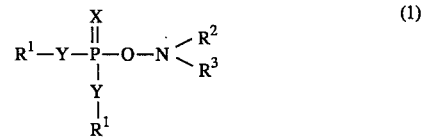

(1)

wherein:

X is a member selected from the group consisting of O and S or is absent, each Y independently is a member selected from the group consisting of O, S and a bond between R1 and P, each $R^1$ independently represents an aliphatic group of up to 10 carbon atoms or the two $R^1$ groups together represent the necessary atoms to complete a 5, 6 or 7-membered ring, $R^2$ and $R^3$ are independently members of the group consisting of hydrogen, cyclic groups and acyclic groups or $R^2$ and $R^3$ together represent the necessary atoms to complete a heterocyclic ring.

16. The photographic element according to claim 15 wherein said gelatin layer is a photographic silver halide layer.

17. The photographic element according to claim 16 wherein said element is a diffusion transfer printing plate.

18. The photographic element according to claim 16 wherein $R^1$ represents an alkyl group of 1 to 5 carbon atoms.

19. The photographic element according to claim 18 wherein Y is O.

20. The photographic element according to claim 16 wherein $R^2$ and $R^3$ are members selected from the group consisting of hydrogen, alkyl of 1 to 5 carbon atoms and acyl.

21. A method according to claim 16 wherein —$NR^2R^3$ is a member selected from the group consisting of succinimide, maleimide and 2-pyridone.

* * * * *

UNITED STATES PATENT AND TRADEMARK OFFICE
CERTIFICATE OF CORRECTION

PATENT NO. : 5,470,699
DATED : November 28, 1995
INVENTOR(S) : Beck et al.

It is certified that error appears in the above-indentified patent and that said Letters Patent is hereby corrected as shown below:

Column 17, line 28, delete "3 8 gm$^{-2}$" and insert --3.8 gm$^{-2}$--.
Column 21, line 53, delete "Domberg" and insert --Domberg--.
Column 24, line 51, delete "bornberg" and insert --Domberg--.
Column 26, line 31, after the word "or" and before the word "is", insert --X--.

Signed and Sealed this

Eighteenth Day of June, 1996

Attest:

BRUCE LEHMAN

*Attesting Officer*     *Commissioner of Patents and Trademarks*